United States Patent [19]

Preston et al.

[11] 4,355,045
[45] Oct. 19, 1982

[54] ANTI-INFLAMMATORY 1-PHENYLETHANOLAMINE DERIVATIVES PHARMACEUTICAL COMPOSITIONS THEREOF AND PROCESSES FOR THEIR MANUFACTURE

[75] Inventors: John Preston; Austin J. Reeve, both of Macclesfield, England

[73] Assignee: Imperial Chemical Industries Limited, London, England

[21] Appl. No.: 930,859

[22] Filed: Aug. 3, 1978

[30] Foreign Application Priority Data

Aug. 16, 1977 [GB] United Kingdom ............... 34346/77

[51] Int. Cl.$^3$ .................... A01N 47/28; A01N 37/18
[52] U.S. Cl. ............................. 424/322; 260/501.17; 260/501.18; 260/404.5; 424/316; 424/324; 564/47; 564/48; 564/56; 564/99; 564/123; 564/168; 564/170; 564/178; 564/182; 564/185; 564/189; 564/190; 564/220
[58] Field of Search ............. 260/558 R, 558 A, 404.5; 424/324, 322; 564/47, 48, 56, 99, 123, 168, 170

[56] References Cited

U.S. PATENT DOCUMENTS 3,536,712 10/1970 Keck et al. ................... 260/570.6 X
3,944,611 3/1976 Smith .................................. 260/562
3,975,443 8/1976 Harper et al. ....................... 260/558

OTHER PUBLICATIONS

Burger, "Medicinal Chemistry", 3rd Ed., Part II, pp. 953–954, (1970).

Primary Examiner—Robert V. Hines
Attorney, Agent, or Firm—Cushman, Darby & Cushman

[57] ABSTRACT

The invention relates to topically anti-inflammatory 1-phenylethanolamine derivatives of the general formula I:

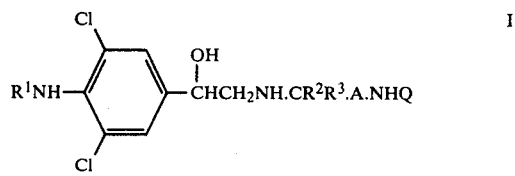

or acid-addition salts thereof, to pharmaceutical compositions thereof, and to analogy processes for their manufacture. A representative compound is 1-(4-amino-3,5-dichlorophenyl)-2-[1,1-dimethyl-2-(2-phenylacetamido)ethylamino]ethanol. The derivatives are useful in particular for the treatment of inflammatory diseases or conditions of the skin.

7 Claims, No Drawings

ANTI-INFLAMMATORY 1-PHENYLETHANOLAMINE DERIVATIVES PHARMACEUTICAL COMPOSITIONS THEREOF AND PROCESSES FOR THEIR MANUFACTURE

This invention relates to 1-phenylethanolamine derivatives which possess anti-inflammatory activity when applied topically to an area of inflammation, and in addition it relates to pharmaceutical compositions of, methods of manufacture of, and methods of treatment using such derivatives.

It is known that 1-phenylethanolamine derivatives such as 1-(4-amino-3,5-dichlorophenyl)-2-t-butylamino ethanol (which is known as clenbuterol) possess potent adrenergic β-receptor stimulatory properties. (Von G Engelhardt, Arzneimittelforschung, 1976, 26, 1403–1420). It is also known (UK patent specification Ser. No. 1,468,156) that 1-phenylethanolamine derivatives such as 1-phenyl-2-[1,1-dimethyl-2-(2-phenylacetamido)ethylamino]ethanol possess adrenergic β-receptor stimulatory properties. We have now discovered, and herein lies our invention, that certain 1-phenylethanolamine derivatives which contain structural features of these known derivatives surprisingly possess useful anti-inflammatory activity when applied topically to an area of inflammation.

According to the invention there is provided a 1-phenylethanolamine derivative of the formula:

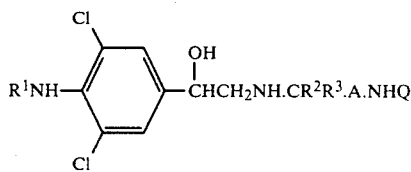

wherein $R^1$ is hydrogen or a $C_{2-6}$-alkanoyl radical; $R^2$ and $R^3$, which may be the same or different, are hydrogen or $C_{1-4}$-alkyl radicals; A is a $C_{1-4}$-alkylene diradical; and Q is a $C_{4-20}$-alkanoyl radical, or a phenylacetyl, phenoxyacetyl or phenylaminocarbonyl radical optionally bearing an aromatic substituent selected from halogen atoms, methyl, methoxy and trifluoromethyl radicals; or a pharmaceutically acceptable acid-addition salt thereof.

It will be observed that, depending on the nature of its substituents, a compound of formula I possesses one or more asymmetric carbon atoms, and can therefore exist in one or more racemic, and two or more optically-active forms. This invention relates to the racemic form of a compound of formula I and to any optically-active form which possesses anti-inflammatory activity, it being well known in the art how to prepare optically active forms by resolution of the racemic form, or by synthesis from optically-active starting materials, and how to determine the anti-inflammatory activity by the standard tests described hereinbelow.

A particular value for $R^1$ when it is a $C_{2-6}$-alkanoyl radical is, for example, a 2,2-dimethylpropionyl (pivaloyl) or 3,3-dimethylbutyryl radical.

A particular value for $R^2$ or $R^3$ when it is a $C_{1-4}$-alkyl radical is, for example, a methyl radical.

A particular value for A is, for example, a methylene, ethylene, ethylidene or isopropylidene diradical, of which a methylene diradical is especially preferred.

A particular value for Q when it is a $C_{4-20}$-alkanoyl radical is, for example, an octadecanoyl (stearoyl) radical.

A particular value for a halogen atom when present as an optional substituent as part of radical Q is, for example, a fluorine, chlorine or bromine atom.

Specific values for Q are, for example, when it is an octadecanoyl, phenylacetyl, 4-methylphenylacetyl, 4-chlorophenylacetyl, phenoxyacetyl, 3-(trifluoromethyl)phenoxyacetyl, 4-methoxyphenoxyacetyl or phenylaminocarbonyl radical.

Particular groups of compounds of formula I are comprised by the following:

(a) those compounds of formula I wherein $R^1$ is hydrogen, $R^2$ and $R^3$, which may be the same or different, are hydrogen or methyl radicals, A is a methylene diradical, and Q has any of the meanings defined above;

(b) those compounds of formula I wherein $R^1$ is hydrogen, $R^2$ and $R^3$ are both hydrogen or methyl radicals, A is a methylene diradical, and Q is a phenylacetyl, phenoxyacetyl, phenylaminocarbonyl or octadecanoyl radical;

(c) those compounds of formula I wherein $R^1$ is a $C_{2-6}$-alkanoyl radical, and $R^2$, $R^3$, A and Q have any of the meanings defined hereinbefore;

and in each group, together with the pharmaceutically acceptable acid-addition salts thereof.

Of these particular groups, that defined in (b) is especially preferred.

A particular acid-addition salt of a compound of formula I is, for example, a salt derived from an acid having a pharmaceutically acceptable anion, for example from an inorganic acid, for example hydrochloric, hydrobromic, phosphoric or sulphuric acid, or from an organic acid, for example oxalic, tartaric, lactic, fumaric, citric, acetic, salicylic, benzoic, β-naphthoic, methane sulphonic or adipic acid. These salts may contain one or two molecular equivalents of acid.

Specific compounds of the invention are described in the accompanying Examples. Of these a particularly preferred compound is 1-(4-amino-3,5-dichlorophenyl)-2-[1,1-dimethyl-2-(2-phenylacetamido)-ethylamino]ethanol; or a pharmaceutically acceptable acid-addition salt thereof.

The compounds of formula I may be manufactured by any process known to be useful for the preparation of chemically analogous compounds. Such processes are provided as a further feature of the invention and are illustrated by the following in which $R^1$, $R^2$, $R^3$, A and Q have any of the meanings defined hereinbefore.

(a) An aryl ketone of the formula:

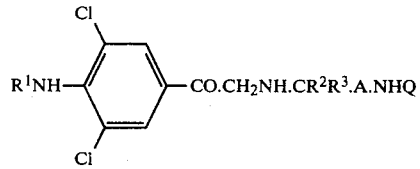

is reduced.

The reduction may be carried out using any agent generally known for reducing aromatic ketones, but which is compatible with the other substituents present in the starting material of formula II. Thus the reduction may be carried out by means of an alkali metal borohydride, for example sodium borohydride, in an appropriate diluent or solvent, for example methanol, ethanol or 2-propanol, or by means of catalytic hydrogenation, for example with hydrogen in the presence of a palladium, platinum or nickel catalyst, in a diluent or solvent, for example ethanol or acetic acid, and in either case, at a temperature of, for example, −20° to 50° C., and conveniently at or near normal room temperature, for example at 15° to 30° C.

The starting materials of formula II may be obtained by reacting a phenacylhalide of the formula:

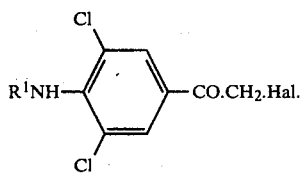

wherein Hal. is a chlorine or a bromine atom, with an amino compound of the formula:

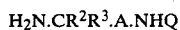

This reaction is conveniently carried out at or near normal room temperature, for example at 15° to 30° C., and in a diluent or solvent, for example, ethanol, dioxan, chloroform or acetonitrile. It may also be carried out in the presence of an acid-binding agent, for example pyridine, triethylamine an alkali metal carbonate or bicarbonate, or in an excess of the amino compound of formula IV.

The starting materials of formula III may themselves be obtained by conventional halogenation of the corresponding acetophenone of formula III, but wherein Hal, is replaced by hydrogen, for example, as described in the accompanying Examples. Equally, the amino starting materials of formula IV may be obtained by conventional selective acylation of a diamine of formula IV but wherein Q is replaced by hydrogen, with an acylating agent derived structurally from an acid of the formula Q.OH, for example, by dropwise addition of the diamine to an excess of acylating agent in a solvent, for example ether, in which the hydrochloride of the compound of formula IV is insoluble.

The starting materials of formula II may conveniently be obtained and used in process
  (a) in the same reaction vessel without separate isolation and purification.
  (b) An aldehyde of the formula:

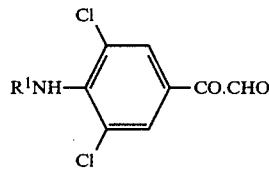

or a hydrate or hemiacetal thereof, is reacted with an amine of formula IV under reducing conditions.

Particularly suitable reducing conditions are provided by using, for example, an alkali metal borohydride or cyanoborohydride, for example sodium borohydride or cyanoborohydride. The process is conveniently carried out in a diluent or solvent, for example, acetonitrile, methanol, ethanol or 2-propanol and at a temperature for example, in the range −20° to 30° C. When sodium cyanoborohydride is used, the reaction is preferably carried out at or near pH4, for example in the presence of acetic acid.

It will be understood that process (b) is an example of the general process known as reductive alkylation, and proceeds at least in part through an intermediate of the formula:

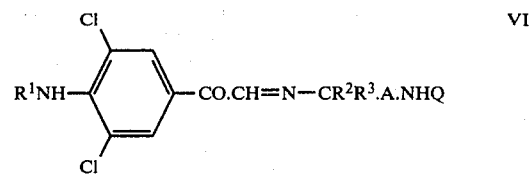

and that process (b) may therefore be carried out by separate steps involving the preparation and subsequent reduction of an intermediate of formula VI.

The starting aldehydes of formula V are conveniently obtained as described in the accompanying Example by selenium dioxide oxidation of the appropriate acetophenone of formula III (Hal.=H), or by dimethylsulphoxide oxidation of the appropriate phenacyl bromide of formula III (Hal.=Br), in each case under conventional conditions.

(c) A compound of the formula:

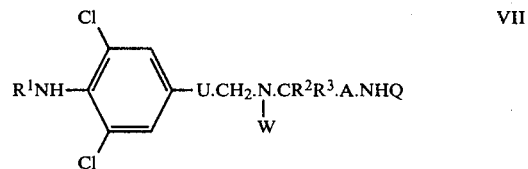

wherein U is a carbonyl or hydroxymethylene diradical, and W is a reductively removable protecting group, is reduced.

A particularly suitable reductively removable protecting group is, for example a benzyl radical. The reduction is preferably carried out by means of catalytic hydrogenation, for example with hydrogen in the presence of a palladium, platinum or nickel catalyst, in a diluent or solvent, for example ethanol or water, or a mixture thereof. The reduction may be carried out at, for example, 15°–35° C. and, may optionally be performed under a pressure of hydrogen of, for example, up to 5 Kg./cm².

It is to be understood that the conditions necessary for removal of the protecting group W in the above process, also result in the reduction of a carbonyl radical U when present in the starting material of formula VII.

Those starting materials of formula VII wherein U is a hydroxymethylene diradical may be obtained, for example, by sodium borohydride reduction of the corresponding aryl ketone of the formula:

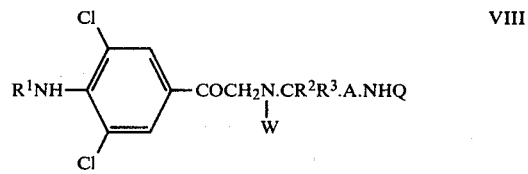

wherein W has the meaning defined above using similar conditions to those described hereinabove in (a), and are conveniently prepared and used in process (c) in the same vessel, without the need for isolation and purification.

The aryl ketones of formula VIII (which are also starting materials of formula VI wherein U is a carbonyl radical) are themselves obtained by reaction of the appropriate phenacyl halide of formula III with an amino compound of the formula:

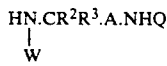
IX wherein W has the meaning defined above, using analogous conditions to those described for the preparation of compounds of formula II in (a) hereinabove. The amino starting materials of formula IX may be obtained by selective acylation of an amine of the formula:

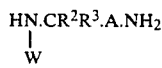
X (itself obtained by standard procedures known in the art), using an acylating agent structurally derived from an acid of the formula Q.OH, for example an acid chloride or bromide, and using known general procedures. Alternatively, when W is a benzyl radical, the starting materials of formula IX are preferably obtained by reductive alkylation of an amine of formula IV using benzaldehyde and sodium borohydride and by analogy with process (b) hereinabove.

Optically-active forms of a compound of formula I may be obtained, for example, by conventional resolution of the corresponding racemic form of a compound of formula I. Thus a racemic form of a compound of formula I is reacted with an optically-active acid, followed by fractional crystallisation of the diastereoisomeric mixture of salts thus obtained from a diluent or solvent, for example ethanol, whereafter the the optically-active form of the compound of formula I is liberated by treatment with base under mild conditions. A particularly suitable optically-active acid is, for example, (+)- or (−)-O,O-di-p-toluoyltartaric acid.

A compound of formula I in free base form may be converted into a pharmaceutically acceptable acid-addition salt by reaction with a suitable acid as defined hereinbefore under conventional conditions.

As stated above, the compounds of formula I possess anti-inflammatory activity when applied topically to an area of inflammation, and are particularly useful in treating by topical administration, inflammatory diseases or inflammatory conditions of the skin.

The anti-inflammatory properties of a compound of formula I may be demonstrated in a standard test involving the inhibition of croton oil induced inflammation on the mouse ear. The activity of an individual compound of formula I in this test depends upon its particular chemical structure, but specific compounds of formula I as described herein produce a significant inhibition of the inflammation at a topically applied dose of 0.20 mg. per ear, or less.

No overt toxic effects were detected at the active doses in the above test.

When used for the topical treatment of an area of inflammation affecting the skin of a warm-blooded animal, for example man, a compound of the invention may be administered topically at a total daily dose in the range 20 µg. to 15 mg., or at an equivalent dose of a pharmaceutically-acceptable acid-addition salt thereof, and conveniently, as a divided dose. It will be appreciated that the total daily amount of a compound of the invention administered depends on the extent and severity of the inflammation to be treated.

As an example of how the invention may be used, when 1-(4-amino-3,5-dichlorophenyl)-2-[1,1-dimethyl-2-(2-phenylacetamido)ethylamino]-ethanol is used for the topical treatment of an area of inflammation affecting the skin of a warm-blooded animal, for example man, a total daily dose in the range of 20 µg. to 5 mg., or an equivalent amount of a pharmaceutically acceptable acid-addition salt, is administered topically.

The compounds of formula I may be administered in the form of pharmaceutical compositions and according to a further feature of the invention there is provided a pharmaceutical composition comprising a compound of formula I, or a pharmaceutically acceptable acid-addition salt thereof, in association with a pharmaceutically acceptable diluent or carrier, and in a form suitable for topical administration. A pharmaceutical composition according to this aspect of the invention may contain from 0.1% to 10% w/w of a compound of formula I or an equivalent amount of a pharmaceutically acceptable acid-addition salt thereof, hereinafter referred to as the active ingredient.

In particular, a pharmaceutical composition according to the invention may be in the form of an ointment, gel, aqueous or oily solution or suspension, emulsion or aerosol. The compositions may be made by methods well known in the art using conventional pharmaceutically acceptable diluents or carriers, together with conventional colouring chelating and preserving agents.

A suitable ointment formulation may be prepared by dispersing the active ingredient in a suitable organic diluent, for example soft paraffin, optionally in the presence of an emulsifying and/or thickening agent, for example sorbitan monostearate.

A suitable gel formulation may be prepared by adding a gelling agent, for example carboxy-polymethylene, to a solution of the active ingredient in a suitable organic solvent, for example isopropyl alcohol.

A suitable emulsion formulation, for example a cream or a lotion, may be prepared by mixing the active ingredient with a suitable conventional emulsifying system and water.

When used in particular for the treatment of inflammatory diseases or conditions of the skin, a composition according to the invention may comprise in addition to the active ingredient defined above, one or more pharmaceutical agents selected from corticosteroids, for example flucinolone acetonide, prednisolone, flumethasone pivalate, betamethasone valerate, hydrocortisone or dexamethasone; phosphodiesterase inhibitors, for example theophylline or caffeine; antibacterial agents, for example oxytetracycline, gentamicin neomycin, gramicidin, chlorhexidine or cetyltrimethylammonium bromide; anti-fungal agents, for example griseofulvin or nystatin; antihistamines, for example diphenhydramine or chlorphenyramine; local anaesthetics, for example amylocaine, benzocaine or procaine and emollients, for example calomine.

Although the compounds of formula I are envisaged to be useful primarily in the topical treatment of inflammatory diseases or conditions of the skin, they may also be useful in the topical treatment of such diseases or conditions which affect other areas of the body, such as those affecting the lungs.

The invention is illustrated but not limited by the following Examples in which:

(i) unless otherwise stated, all procedures were carried out at room temperature, that is at a temperature in the range 18°–26° C.; and all evaporations were performed by rotary evaporation;

(ii) petroleum ether fractions are referred to as "petrol" and the appropriate boiling range is given in parentheses; and (iii) yields, where given, are purely illustrative and are not to be construed as limiting.

EXAMPLES 1–2

A mixture of 4-amino-3,5-dichlorophenylglyoxal hydrate (1.18 g.) and 1,1-dimethyl-2-(2-phenylacetamido)ethylamine (1.03 g.) in methanol (20 ml.) was stirred at room temperature for 16 hours. The mixture was then filtered and the filtrate stirred vigorously during the dropwise addition of a solution of sodium borohydride (500 mg.) in water (2 ml.). After stirring for 2 hours, the mixture was acidified with concentrated hydrochloric acid to pH 2–3, and then evaporated. The solid residue was suspended in water (50 ml.) and the suspension obtained was extracted with ether (100 ml). The aqueous phase was basified to pH 12–13 by addition of aqueous ammonia solution (density 0.88), and extracted with ether ($2\times100$ ml.). The combined extracts were dried ($MgSO_4$) and evaporated. The resultant oil was dissolved in propan-2-ol (5 ml.) and an ethereal solution of hydrogen chloride was added to bring the pH to 2–3. Further addition of an excess of dry ether gave a precipitate (1.05 g., 43%) of 1-(4-amino-3,5-di-chlorophenyl)-2-[1,1-dimethyl-2-(2-phenylacetamido)ethylamino]-ethanol dihydrochloride (Example 1), m.p. 105°–8° C.

In a similar manner but using 1,1-dimethyl-2-(2-phenoxyacetamido)ethylamine and 4-amino-3,5-dichlorophenylglyoxal hydrate as starting materials there was obtained 1-(4-amino-3,5-dichlorophenyl)-2-[1,1-dimethyl-2-(2-phenoxyacetamido)ethylamino]-ethanol (Example 2) in 35% yield, m.p. 107°–9° C. (hydrochloride, monohydrate).

The starting materials were obtained in the following manner:

(a) 1,1-Dimethyl-2-(2-phenylacetamido)ethylamine:

A solution of 1,1-dimethylethylenediamine (8.8 g.) in ether (250 ml.) was added during 2 hours to a stirred solution of phenylacetyl chloride (15.4 g.) in ether (250 ml.). This mixture was further stirred for 2 hours. The solid was separated by filtration, and dissolved in warm water (150 ml.). The solution obtained was filtered. The filtrate was basified by addition of an excess of saturated aqueous sodium carbonate solution (50 ml.), and then extracted with chloroform ($3\times250$ ml.). The extracts were dried ($MgSO_4$) and evaporated to give an oil which crystallised on addition of a 1:1 v/v mixture of ether and petrol (60°–80°) to give 1,1-dimethyl-2-(2-phenylacetamido)ethylamine (13.1 g., 63%), m.p. 47°–48° C.

(b) 1,1-Dimethyl-2-(2-phenoxyacetamido)ethylamine:

This compound was obtained as a solid, m.p. 42°–46° C., in an analogous manner to that described above for (a) but using phenoxyacetyl chloride as starting material.

(c) 4-Amino-3,5-dichlorophenylglyoxal hydrate:

To a solution of 4-amino-3,5-dichloroacetophenone (12.0 g.) in a mixture of dioxan (60 ml.) and water (2 ml.), was added selenium dioxide (10.0 g.). The solution was heated at 95° C. on a steam bath for 4 hours. The precipitate was then separated by filtration and the filtrate was evaporated. The resulting oil was repeatedly dissolved in toluene and evaporated to remove water and the residue was dissolved in ether (500 ml.). Decolourising charcoal was added to the ethereal solution and after filtration the solution was concentrated to a volume of approximately 200 ml. whereupon 4-amino-3,5-dichlorophenylglyoxal hydrate separated as a solid (8.0 g. 58%), m.p. 95°–98° C.

EXAMPLE 3

A mixture of 1,1-dimethyl-2-(2-phenylacetamido)ethylamine hydrochloride (2.42 g.) and triethylamine (1.4 ml.) in chloroform (50 ml.) was stirred for 5 minutes. 4-Amino-3,5-dichloro-$\alpha$-bromoacetophenone (1.42 g.) was then added. The mixture was then further stirred for 16 hours, evaporated, and the residue obtained was dissolved in water (50 ml.). The aqueous solution was basified by addition of an excess of 10% w/v aqueous sodium carbonate solution, and extracted with ether ($2\times100$ ml.). The combined extracts were dried ($MgSO_4$) and evaporated to give $\alpha$-[1,1-dimethyl-2-(2-phenylacetamido)ethylamino]-4-amino-3,5-dichloroacetophenone which was dissolved without further purification in methanol (20 ml.).

A solution of sodium borohydride (0.5 g.) in water (2 ml.) was added to the methanolic solution and the mixture was stirred for 2 hours. This mixture was then acidified to pH 2–3 with concentrated hydrochloric acid and concentrated in vacuo. The residual solution was diluted with water and then extracted with ether ($3\times100$ ml.). The aqueous phase was then basified to pH 12–13 by addition of aqueous ammonia solution (density 0.88), and extracted with ether ($3\times100$ ml.). These combined extracts were dried ($MgSO_4$) and evaporated to give 1-(4-amino-3,5-dichlorophenyl)-2-[1,1-dimethyl-2-(2-phenylacetamido)ethylamino]-ethanol (Example 3) as an oil which slowly crystallised, to give the solid free base (0.8 g., 39%), which had m.p. 96°–98° C. after purification by conversion to the dihydrochloride salt (as described in Example 1) followed by liberation of the free base by basifying an aqueous solution of the dihydrochloride and solvent extraction.

The 4-amino-3,5-dichloro-$\alpha$-bromoacetophenone was obtained as follows:

A solution of 4-amino-3,5-dichloroacetophenone (21.1 g.) in chloroform (300 ml.) was heated under reflux and treated simultaneously dropwise, with a solution of bromine (16.5 g.) in chloroform (20 ml.), and with absolute ethanol (20 ml.).

After the addition was over, the solution was heated under reflux for 15 minutes and then concentrated by heating in an open flask to a volume of about 50 ml. This solution was cooled in an ice-bath whereupon 4-amino-3,5-dichloro-$\alpha$-bromoacetophenone slowly separated as a crystalline solid (19.5 g., 66%) m.p. 150°–152° C.

EXAMPLE 4

To a solution of 4-amino-3,5-dichloro-$\alpha$-bromoacetophenone (0.85 g.) in dioxan (25 ml.) was added N-benzyl-N'-(phenylacetyl)ethylene diamine (1.61 g.), and the solution was stirred for 16 hours. The solution was then diluted with ether (50 ml.) and washed successively with 10% w/v aqueous sodium carbonate solution (2×50 ml.), water (2×50 ml.) and saturated brine (50 ml.). The ether solution was then dried (MgSO$_4$) and evaporated to give α-[N-benzyl-2-(2-phenylacetamido)ethylamino]-4-amino-3,5-dichloroacetophenone as an oily residue.

This residue was dissolved in methanol (25 ml.) and a solution of sodium borohydride (0.25 g.) in water (2 ml.) was added with vigorous stirring. The resultant solution was stirred for 2 hours, then sufficient concentrated hydrochloric acid was added to bring the pH of the solution to 2-3. The mixture was evaporated and the solid product was dissolved in water (50 ml.). The aqueous solution was extracted with ether (100 ml.) and the extract discarded. The aqueous phase was basified with aqueous ammonia solution (density 0.88) and was again extracted with ether (3×100 ml.). The extracts were combined, dried (MgSO$_4$) and evaporated to give 1-(4-amino-3,5-dichlorophenyl)-2-[N-benzyl-2-(2-phenylacetamido)ethylamino]-ethanol as an oil. This oil was dissolved in ethanol (50 ml.) and 30% w/w palladium-on-charcoal (50 mg.) was added. The mixture was shaken in an atmosphere of hydrogen at atmospheric pressure until the theoretical uptake of gas had occurred. The catalyst was removed by filtration. The filtrate was evaporated to give 1-(4-amino-3,5-dichlorophenyl)-2-[2-(2-phenylacetamido)ethylamino]ethanol as a semi-solid which was isolated as its hydrochloride (0.54 g., 43%), m.p. 118°-20° C., by dissolving the semi-solid in propan-2-ol (5 ml.), adding sufficient of a solution of hydrogen chloride in dry ether to bring the pH to 2-3, and then precipitating the hydrochloride salt by addition of an excess of dry ether.

The N-benzyl-N'-(phenylacetyl)ethylene diamine was prepared as follows:

A mixture of ethyl phenyl acetate (100 g. 0.61 mole) and ethylene diamine (120 ml., 1.86 mole) was heated on a steam bath for 4 days. Excess ethylene diamine was removed under reduced pressure and the residue dissolved in water (500 ml.) and any insoluble material was removed by filtration. Evaporation of the filtrate gave crude N-(2-phenylacetyl)ethylene diamine (96.8 g.) which was used without purification.

Benzaldehyde (67.5 g., (0.637 mole) was added to a solution of N-(2-phenylacetyl)ethylene diamine (113.5 g., 0.637 mole) and the mixture was stirred for 18 hours. Sodium borohydride (24.2 g.) was added in portions and the reaction mixture was stirred for an additional 1.5 hours. Acetic acid was then added until excess borohydride had been destroyed. The reaction mixture was basified by addition of 2 N sodium hydroxide solution and extracted with ethyl acetate (3×500 ml.). The extracts were washed with brine (300 ml.), dried (MgSO$_4$) and filtered. Hydrogen chloride gas was bubbled into the ethyl acetate filtrate until it was acid (pH 2). After 4 hours at 0° C., the precipitate was collected to give N-benzyl-N'-(phenylacetyl)ethylene diamine hydrochloride (46.2 g.), m.p. 183°-185° C.

The free base was liberated from the hydrochloride (15 g.) by basification of a solution in water (150 ml.) with solid sodium carbonate. The aqueous mixture was extracted with ethyl acetate (3×100 ml.) and the extracts were dried (MgSO$_4$) and evaporated to give N-benzyl-N'-(phenylacetyl)ethylene diamine as an oil (13.0 g.), which slowly crystallised.

EXAMPLE 5

A mixture of 4-amino-3,5-dichlorophenylglyoxal hydrate (1.16 g.) and 1,1-dimethyl-2-(stearoylamino)ethylamine (1.77 g.) in methanol (25 ml.) was stirred for 16 hours, during which time a white solid gradually precipitated. The stirred suspension was then treated dropwise with a solution of sodium borohydride (500 mg.) in water (5 ml.). During this addition the white solid dissolved to give a clear solution. After stirring for 2 hours the mixture was acidified with acetic acid to pH 5 and then evaporated.

The solid residue obtained was suspended in water (50 ml.) and the suspension obtained was extracted with ether (2×50 ml.). The extracts were combined, dried (MgSO$_4$) and evaporated to give an oil, which was dissolved in ether (25 ml.). The solution obtained was cooled to give 1-(4-amino-3,5-dichlorophenyl)-2-[1,1-dimethyl-2-(stearoylamino)ethylamino]ethanol (0.9 g., 40%), m.p. 74°-76° C.

The starting ethylamine derivative was obtained as follows:

A solution of 1,1-dimethylethylene diamine (3.6 g.) in ether (100 ml.) was added during 2 hours to a stirred solution of stearoyl chloride (12.12 g.) in ether (250 ml.) and the mixture was further stirred for 1 hour. The solid which formed was separated and dissolved in hot water (300 ml.). The solution obtained was filtered and the filtrate was basified by addition of an excess of saturated aqueous sodium carbonate solution (30 ml.) to give 1,1-dimethyl-2-(stearoylamino)ethylamine (8.0 g.) m.p 56°-58° C. (after washing with water, and air drying).

EXAMPLE 6

A mixture of 4-amino-3,5-dichlorophenylglyoxal hydrate (1.77 g.) and 1,1-dimethyl-2-(phenylureido)ethylamine (1.55 g.) in methanol (30 ml.) was stirred for 30 minutes. The mixture was then treated dropwise with a solution of sodium borohydride (750 mg.) in water (5 ml.). After stirring for a further two hours, the mixture was acidified with acetic acid to pH 5 and then evaporated. The solid residue was suspended in water (50 ml.) and the suspension obtained was extracted with ether (2×100 ml.). The combined extracts were dried (MgSO$_4$), and evaporated to give an oil which has dissolved in propan-2-ol (5 ml.). Ethereal hydrogen chloride was added to the solution obtained to bring the pH to 2-3, followed by dry ether until 1-(4-amino-3,5-dichlorophenyl)-2-[1,1-dimethyl-2-(phenylureido)ethylamino]ethanol hydrochloride deposited as a solid, which was recrystallised from methanol and ether to give pure material (1.2 g., 36%), m.p. 197°-198° C.

The starting ethylamine derivative was obtained as follows:

A solution of phenyl isocyanate (11.9 g.) in ether (250 ml.) was added dropwise over 2 hours to a stirred solution of 1,1-dimethylethylene diamine (8.8 g.) in ether (250 ml.). After a further 2 hours stirring the mixture was separated by filtration and the solid product was shaken with an exesss of N-hydrochloric acid. The insoluble di-urea derivative was removed by filtration. The filtrate was basified by addition of an excess of saturated aqueous sodium carbonate solution, to give 1,1-dimethyl-2-(phenylureido)ethylamine (6.5 g.), m.p. 124°-126° C. (after washing with water and air drying.)

EXAMPLE 7

1,1-Dimethyl-2-(2-phenylacetamido)ethylamine (1.03 g.) was added to a solution of 4-pivaloylamino)-3,5-dichlorophenylglyoxal hydrate (1.6 g.) in methanol (50 ml.). The solution was stirred for 2 hours and then a solution of sodium borohydride (500 mg.) in water (5 ml.) was added. After a further 2 hours of stirring, sufficient acetic acid was added to bring the pH to 4–5. The solution was then evaporated and the residue was dissolved in water (50 ml.). The aqueous solution was extracted with ether (2×50 ml.) and then basified using 10% w/v aqueous sodium carbonate solution to give 1-[4-(pivaloylamino)-3,5-dichlorophenyl]-2-[1,1-dimethyl-2-(2-phenylacetamido)ethylamino]ethanol (0.8 g., 32%), m.p. 83°–85° C.

The necessary ethylamine derivative was obtained as follows:

4-(Pivaloylamino)-3,5-dichloroacetophenone (2.6 g.) was added to a solution of selenium dioxide (2.5 g.) in a mixture of dioxan (30 ml.) and water (1 ml.). The solution was heated at 90° C. for 3 hours, cooled, the precipitated selenium metal removed by filtration, and the subsequent filtrate evaporated. The oil obtained was purified by chromatography on a silica gel column using 3% v/v ethanol in chloroform as eluant to give 4-(pivaloylamino)-3,5-dichlorophenylglyoxal hydrate as an oil (1.2 g.) which was used without further purification.

The acetophenone derivative was itself obtained as follows:

4-Amino-3,5-dichloroacetophenone (2.0 g.) was added to a mixture of pivalic anhydride (15 ml.) and pivaloyl chloride (2 ml.), and the solution was heated under reflux for 3 hours, then cooled, and poured into an excess of 10% w/v aqueous sodium carbonate solution (100 ml.). The mixture obtained was stirred for 2 hours and then extracted with ether (3×100 ml.). The combined extracts were dried (MgSO₄) and evaporated to give an oil which was dissolved in ether (20 ml.). The solution obtained was diluted with petrol (60–80) (150 ml.) to give 4-(pivaloylamino)-3,5-dichloroacetophenone (2.6 g.), m.p. 137°–139° C.

EXAMPLE 8

A mixture of 4-amino-3,5-dichlorophenylglyoxal hydrate (2.35 g.) and 1,1-dimethyl-2-(2-phenylacetamido)ethylamine (2.06 g.) in acetonitrile (50 ml.) and acetic acid (3 ml.) was stirred for 30 minutes. Sodium cyanoborohydride (1.26 g.) was then added to the reaction mixture in portions over 5 minutes. After 16 hours of stirring the mixture was evaporated and the residue was partitioned between 10% v/v aqueous acetic acid (100 ml.) and ethyl acetate (100 ml.). The organic phase was separated, dried (MgSO₄) and evaporated. The semi-solid residue was dissolved in propan-2-ol (10 ml.) and ethereal hydrogen chloride was added to bring the pH to 2–3. Addition of dry ether then gave a precipitate (2.8 g., 63%) of 1-(4-amino-3,5-dichlorophenyl)-2-[1,1-dimethyl-2-(2-phenylacetamido)ethylamino]ethanol dihydrochloride m.p. 105°–108° C.

The free base form (m.p. 96°–98° C.) was obtained by adding the dihydrochloride to an excess of 10% v/v aqueous sodium carbonate and ether, and separation and evaporation of the dried (MgSO₄) extracts.

EXAMPLE 9

A mixture of finely powdered 1-(4-amino-3,5-dichlorophenyl)-2-[1,1-dimethyl-2-(2-phenylacetamido)ethylamino]ethanol hydrochloride (0.5 w/w) in liquid paraffin (10 w/w) was added to molten white soft paraffin (89.5 w/w). The resultant mixture was cooled to room temperature with fast stirring until a uniformly dispersed ointment was obtained, suitable for therapeutic use.

In a similar manner an ointment containing as active ingredient a compound described in Example 2, 4, 5, 6 or 7 or the free base described in Example 8 may be obtained.

EXAMPLE 10

A solution of 1-(4-amino-3,5-dichlorophenyl)-2-[1,1-dimethyl-2-(2-phenylacetamido)ethylamino]ethanol hydrochloride (or the free base) (0.1 w/w) in propan-2-ol (30 w/w) was mixed with water (66.9 w/w) with rapid stirring and further addition of "Carbopol" 940* (3 w/w) until a highly dispersed gel, suitable for therapeutic use, was obtained.

Using a similar procedure a gel containing as active ingredient a compound described in Example 2, 4, 5, 6 or 7 may be obtained.

*"Carbopol" 940 is a grade of carboxypolymethylene gelling agent available from B. F. Goodison Chemical Co., Cleveland, Ohio, USA; "Carbopol" is a trade-mark.

EXAMPLE 11

A mixture of cetostearyl alcohol (9 w/w), liquid paraffin (7 w/w), sorbitan monstearate (2 w/w), polysorbate (60 w/w) and finely powdered 1-(4-amino-3,5-dichlorophenyl)-2-[1,1-dimethyl-2-(2-phenylacetamido)ethylamino]ethanol hydrochloride (or the free base) (0.1 w/w) was fused together at 65°–70° C. Water (79.9 w/w) was then added with rapid stirring and the mixture was slowly cooled to room temperature to give a homogeneous cream suitable for therapeutic use.

Using a similar process, there may be obtained a cream containing as active ingredient a compound described in Example 2, 4, 5 or 7.

What is claimed is:

1. A 1-phenylethanolamine derivative of the formula:

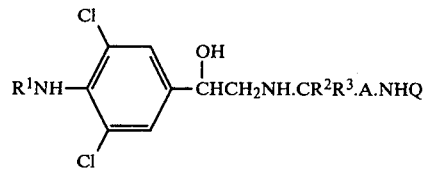

wherein $R^1$ is hydrogen; $R^2$ and $R^3$ are both hydrogen or methyl; A is methylene; and Q is phenylacetyl, phenoxyacetyl, phenylaminocarbonyl or octadecanoyl; or a pharmaceutically acceptable acid-addition salt thereof.

2. A 1-phenylethanolamine derivative selected from the group consisting of 1-(4-amino-3,5-dichlorophenyl)-2-[1,1-dimethyl-2-(2-phenylacetamido)ethylamino]ethanol; and the pharmaceutically acceptable acid-addition salts thereof.

3. An acid-addition salt claimed in claim 1 in which the acid is selected from the group consisting of hydrochloric, hydrobromic, phosphoric, sulphuric, oxalic, tartaric, lactic, fumaric, citric, acetic, salicyclic, benzoic, β-naphthoic, methanesulphonic and adipic acid.

4. A pharmaceutical composition for use in the topical treatment of inflammation comprising a 1-phenylethanolamine derivative of formula I, or a pharmaceutically acceptable acid-addition salt, as defined in claim 1, in association with a pharmaceutically acceptable diluent or carrier, and in a form suitable for topical administration.

5. A composition claimed in claim 1, which is in a form selected from an ointment, gel, aqueous solution, aqueous suspension, oily solution, oily suspension, emulsion and aerosol form.

6. A method of topical treatment of an area of inflammation in a warm-blooded animal requiring such treatment, which comprises administering topically an effective amount of a 1-phenylethanolamine derivative of formula I, or of a pharmaceutically acceptable acid-addition salt thereof, as defined in claim 1, to said area of inflammation affecting said animal.

7. A method as claimed in claim 6 in which the 1-phenylethanolamine derivative is selected from 1-(4-amino-3,5-dichlorophenyl)-2-[1,1-dimethyl-2-(2-phenylacetamido)ethylamino]-ethanol; and the hydrochloride and hydrobromide thereof.

* * * * *